United States Patent
Tsymbalenko

(10) Patent No.: US 12,004,900 B2
(45) Date of Patent: Jun. 11, 2024

(54) SYSTEM AND METHODS FOR A MEASUREMENT TOOL FOR MEDICAL IMAGING

(71) Applicant: GE Precision Healthcare LLC, Wauwatosa, WI (US)

(72) Inventor: Yelena Tsymbalenko, Mequon, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 348 days.

(21) Appl. No.: 17/343,619

(22) Filed: Jun. 9, 2021

(65) Prior Publication Data
US 2022/0395251 A1 Dec. 15, 2022

(51) Int. Cl.
| A61B 8/08 | (2006.01) |
| A61B 8/00 | (2006.01) |
| G06N 3/04 | (2023.01) |
| G06N 3/08 | (2023.01) |
| G06T 7/00 | (2017.01) |

(Continued)

(52) U.S. Cl.
CPC ............ *A61B 8/0858* (2013.01); *A61B 8/461* (2013.01); *G06N 3/04* (2013.01); *G06N 3/08* (2013.01); *G06T 7/0012* (2013.01); *G06T 7/11* (2017.01); *G16H 15/00* (2018.01); *G16H 30/20* (2018.01); *G16H 30/40* (2018.01); *G16H 50/20* (2018.01); *G16H 50/30* (2018.01); *G16H 50/50* (2018.01); *G06T 2207/10132* (2013.01); *G06T 2207/20081* (2013.01); *G06T 2207/20084* (2013.01); *G06T 2207/30056* (2013.01); *G06T 2207/30168* (2013.01)

(58) Field of Classification Search
CPC ....... A61B 8/0858; A61B 8/461; A61B 8/085; A61B 8/5223; A61B 8/0833; A61B 8/4477; A61B 8/48; A61B 8/5292; G06N 3/04; G06N 3/08; G06N 3/084; G06T 7/0012; G06T 7/11; G06T 2207/10132; G06T 2207/20081; G06T 2207/20084; G06T 2207/30056; G06T 2207/30168; G16H 15/00; G16H 30/20; G16H 30/40; G16H 50/20; G16H 50/30; G16H 50/50
See application file for complete search history.

(56) References Cited

U.S. PATENT DOCUMENTS

2018/0144465 A1* 5/2018 Hsieh ................. G16H 30/40

OTHER PUBLICATIONS

Gur et al., Ultrasonographic visceral fat thickness in the first trimester can predict metabolic syndrome and gestational diabetes mellitus. Endocrine. Nov. 2014;47(2):478-84. doi: 10.1007/s12020-013-0154-1. Epub Jan. 23, 2014. PMID: 24452873.*

(Continued)

*Primary Examiner* — Bo Joseph Peng
(74) *Attorney, Agent, or Firm* — McCoy Russell LLP

(57) ABSTRACT

Methods and systems are provided for evaluating a subject for a liver disease using ultrasound images. In one example, a method includes, in response to a request to evaluate the liver disease, determining, with a measurement model, that a selected medical image frame of the subject includes a target anatomical view and has an image quality above a threshold image quality, and in response, measuring, with the measurement model, a marker for the liver disease in the selected medical image, and outputting, for display on a display device, the measurement of the marker.

6 Claims, 7 Drawing Sheets

(51) Int. Cl.
| | |
|---|---|
| *G06T 7/11* | (2017.01) |
| *G16H 15/00* | (2018.01) |
| *G16H 30/20* | (2018.01) |
| *G16H 30/40* | (2018.01) |
| *G16H 50/20* | (2018.01) |
| *G16H 50/30* | (2018.01) |
| *G16H 50/50* | (2018.01) |

(56) References Cited

OTHER PUBLICATIONS

Pirmoazen et al., Quantitative ultrasound approaches for diagnosis and monitoring hepatic steatosis in nonalcoholic fatty liver disease. Theranostics. Mar. 4, 2020;10(9):4277-4289. doi: 10.7150/thno. 40249. PMID: 32226553; PMCID: PMC7086372.*

Woldemariam, M. et al., "Measuring Abdominal Visceral Fat Thickness with Sonography: A Methodologic Approach," Journal of Diagnostic Medical Sonography, vol. 34, No. 2, Jan. 13, 2018, 6 pages.

Byra, M. et al., "Transfer learning with deep convolutional neural network for liver steatosis assessment in ultrasound images," International Journal of Computer Assisted Radiology and Surgery, vol. 13, No. 12, Dec. 2018, Available Online Aug. 9, 2018, 9 pages.

Angoorani, H. et al., "Is ultrasound-measured abdominal fat thickness a reliable method for predicting metabolic diseases in obese and overweight women?," Medical Journal of the Islamic Republic of Iran, vol. 32, No. 78, Aug. 28, 2018, 6 pages.

* cited by examiner

SYSTEM AND METHODS FOR A MEASUREMENT TOOL FOR MEDICAL IMAGING

TECHNICAL FIELD

Embodiments of the subject matter disclosed herein relate to medical imaging, and more particularly, to an automated measurement tool for evaluating liver disease using medical imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method for evaluating a subject for a liver disease includes, in response to a request to evaluate the liver disease, determining, with a measurement model, that a selected medical image frame of the subject includes a target anatomical view and has an image quality above a threshold image quality, and in response, measuring, with the measurement model, a marker for the liver disease in the selected medical image, and outputting, for display on a display device, the measurement of the marker.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
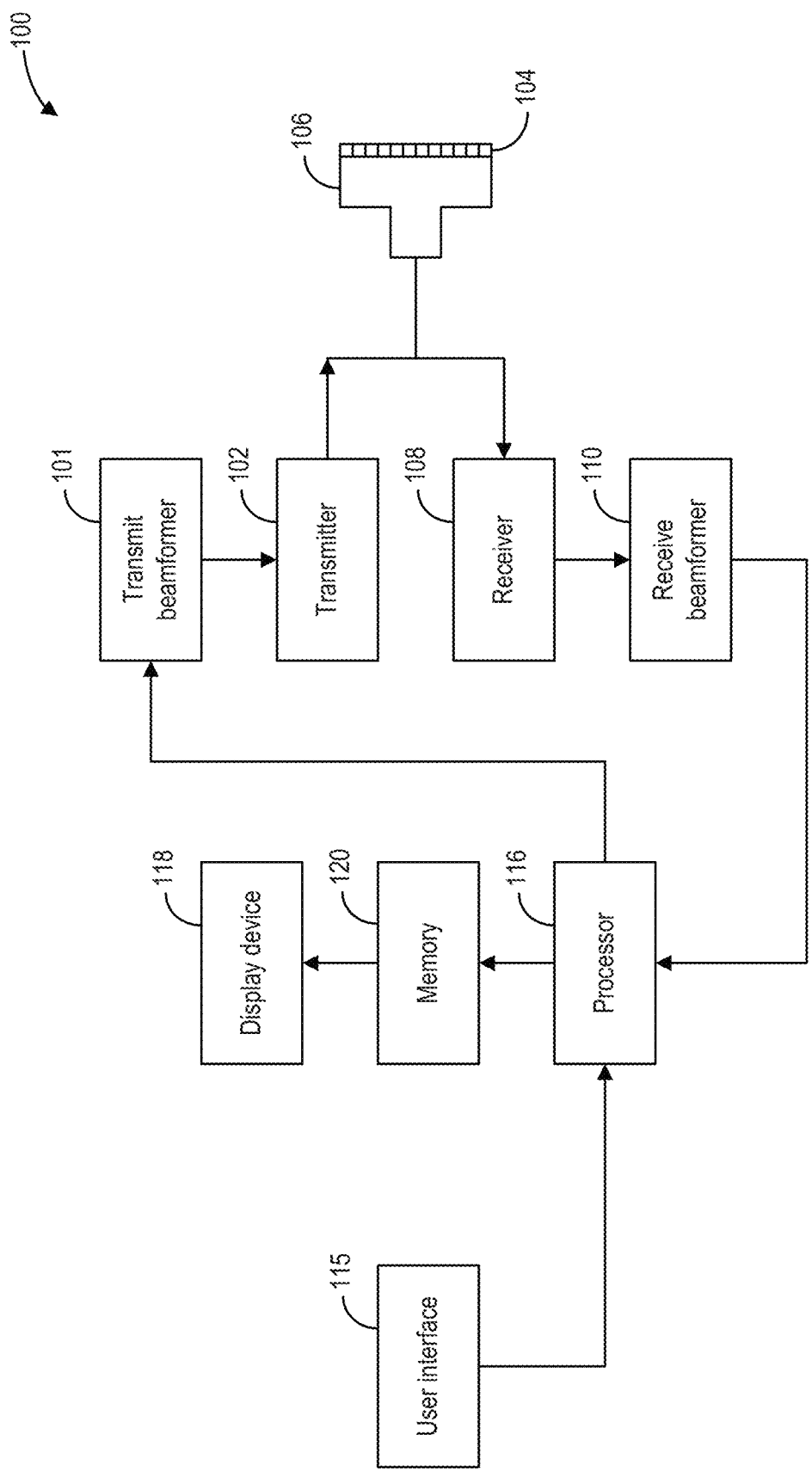
FIG. 1 shows a block diagram of an embodiment of an ultrasound system.

Medical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position of the ultrasound probe in order to obtain high-quality images of one or more target anatomical features (e.g., the heart, the liver, the kidney, or another anatomical feature).

Ultrasound imaging may be preferred over biopsy or other types of medical imaging (e.g., computed tomography or magnetic resonance imaging) for evaluation and monitoring of patient conditions, such as disease progression, due to the relatively inexpensive, portable, non-invasive, and widespread nature of ultrasound imaging. However, the lack of standardization in acquired ultrasound images resulting from operator to operator variation may make diagnosis and/or monitoring of certain conditions challenging. For example, non-alcoholic fatty liver disease (NAFLD), typically found in obese patients, is defined as having accumulation of fat in more than 5% of liver cells and is the most prevalent liver disease. NAFLD is currently diagnosed via a liver biopsy. Liver biopsy is invasive and is not suitable for monitoring disease risk or progression in a large number of prospective or diagnosed patients.

Accordingly, NAFLD is a patient condition that would be well suited for diagnosis and monitoring via ultrasound, in order to aid in early detection and ongoing monitoring of the disease that is currently not possible with liver biopsy. However, diagnosing or monitoring NAFLD by using ultrasound imaging of the liver itself has up until now been challenging given the operator-dependent nature of ultrasound imaging. For example, differences in operator experience level, ultrasound machines, and ultrasound settings may result in varying images of different anatomical views and image quality being acquired and used to monitor or diagnose NAFLD, which may lead to inconsistent and unreliable evaluations of NAFLD. Thus, widespread use of ultrasound to evaluate NAFLD has not been adopted.

Thus, according to embodiments disclosed herein, NAFLD may be diagnosed and staged by measuring abdominal visceral fat using a measurement tool on ultrasound images. The measurement tool may include artificial intelligence classification models (e.g., a measurement model as described below) to detect a standard plane where visceral fat measurements may be taken, measure image quality for visceral fat measurements, process visceral fat measurements including computing an average measurement across a plurality of visceral fat measurements, and predict a risk of a presence of NAFLD based on visceral fat measurements. Measuring abdominal visceral fat to diagnose NAFLD may facilitate early diagnoses of NAFLD by exposing artificial intelligence classification models to a plurality of preliminary or early NAFLD cases, and supplementing visceral fat measurements with artificial intelligence classification models may lead to more accurate tests, measurements, and predictions, including diagnosing NAFLD in patients with no symptoms. By ensuring that a standard plane and high quality images are used for the visceral fat measurement, the measurement model described herein may increase the accuracy of the visceral fat measurement, which may reduce false positive and false negative results and reduce operator to operator variation in the measurements.

Figure 2:
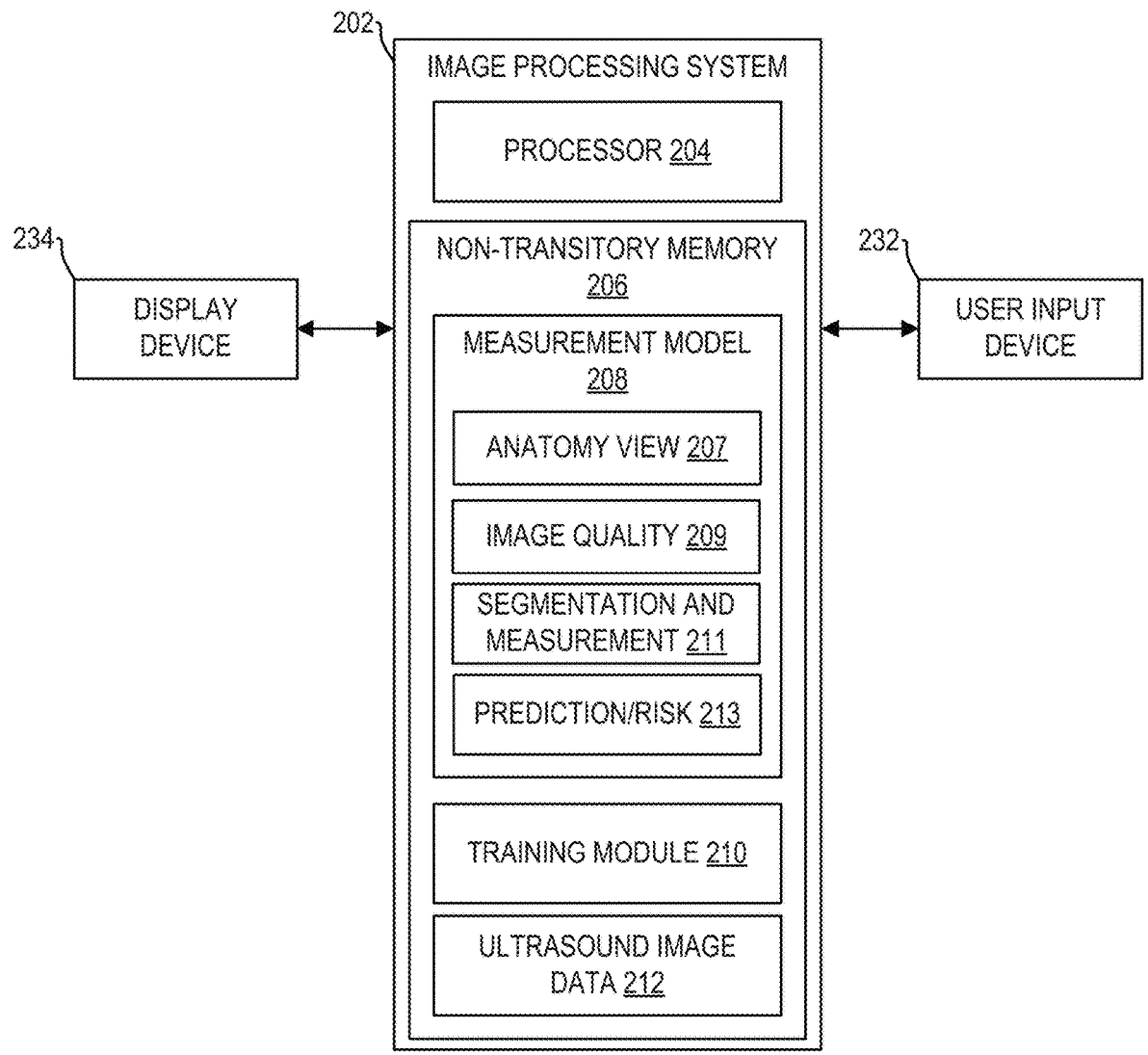
FIG. 2 is a schematic diagram illustrating a system for measuring medical images using a measurement model, according to an embodiment.
Figure 3:
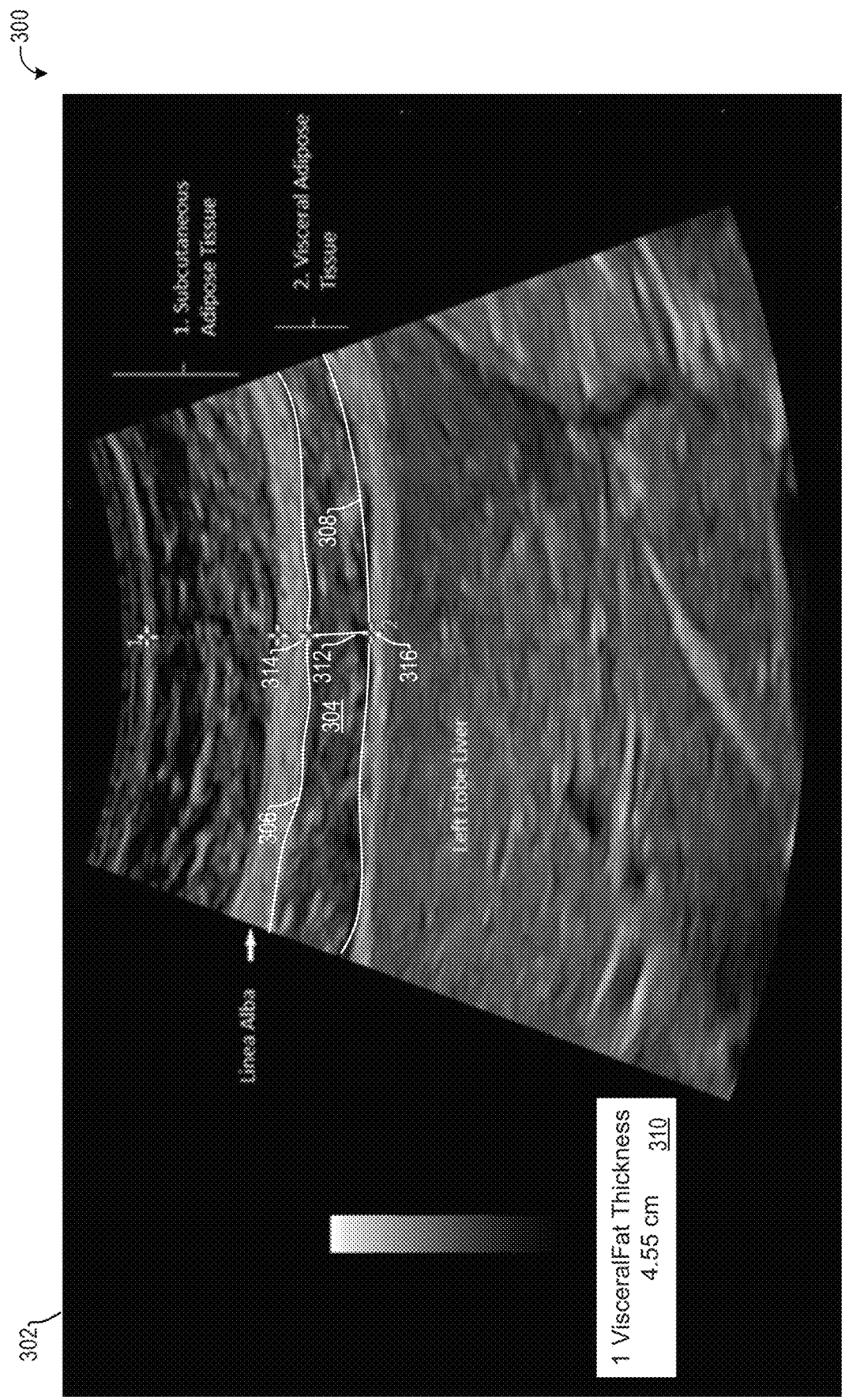
FIGS. 3-5 show an example ultrasound image and corresponding annotations generated via the measurement model.
Figure 4:
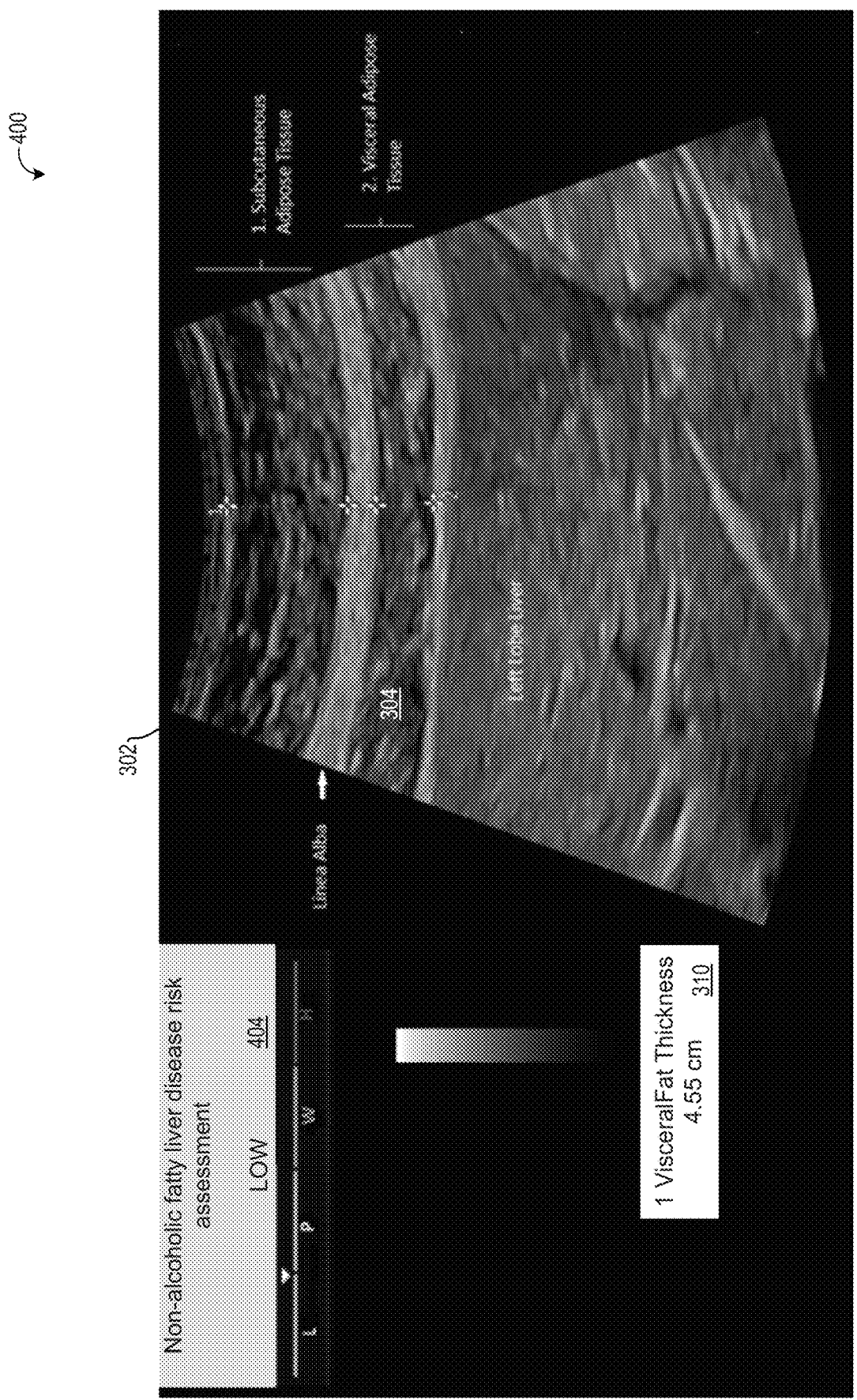
Figure 5:
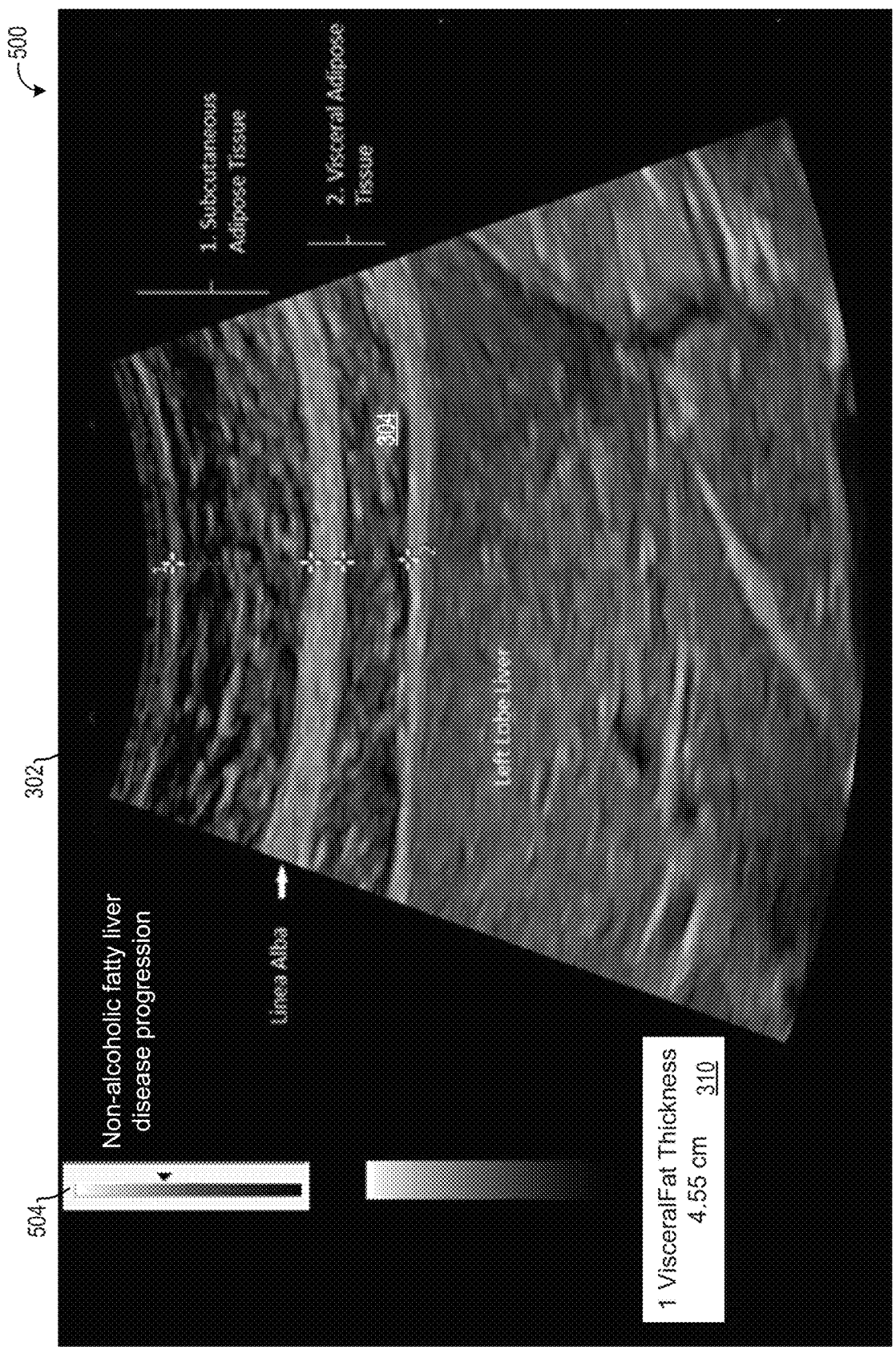

An example ultrasound system including an ultrasound probe, a display device, and an imaging processing system are shown in FIG. 1. Via the ultrasound probe, ultrasound images may be acquired and displayed on the display device. An image processing system, as shown in FIG. 2, includes a measurement model, which may include a plurality of sub-models trained to perform various tasks in order to evaluate liver disease, such as anatomy view detection, image quality detection, anatomy segmentation and measurement, and disease risk/progression analysis, which may be deployed according to method of FIG. 6 and trained according to the method of FIG. 7 in order to evaluate liver disease such as NAFLD. Once the measurement model identifies an image in a target view with sufficient quality, the measurement model may measure a target anatomical feature (herein, visceral fat around the liver) and determine disease risk or progression based on the measured target anatomical feature, and the measurement and disease risk or progression may be displayed along with the image, as shown in FIGS. 3-5.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. A variety of a geometries and configurations may be used for the transducer array (e.g., linear, convex, phased array) and the transducer array may be provided as part of, for example, different types of ultrasound probes, including but not limited to standard hand-held linear or curvilinear probes, endocavity probes, and cardiac probes. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into the body (e.g., of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to perform all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound imaging system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block.

Ultrasound images acquired by ultrasound imaging system 100 may be further processed. In some embodiments, ultrasound images produced by ultrasound imaging system 100 may be transmitted to an image processing system, where in some embodiments, the ultrasound images may be analyzed by one or more machine learning models trained using ultrasound images and corresponding ground truth output in order to estimate the current user action (e.g., the probe motion prior to and/or during acquisition of the current ultrasound image), the current anatomical view in the ultrasound image, and probe motion recommendations. As used herein, ground truth output refers to an expected or "correct" output based on a given input into a machine learning model. For example, if a machine learning model is being trained to classify images of cats, the ground truth output for the model, when fed an image of a cat, is the label "cat". As explained in more detail below, if a machine learning model is being trained to classify ultrasound images on the basis of the probe motion/user action occurring prior to and/or during acquisition of the ultrasound image, the ground truth output for the model may be a label indicating the probe motion/user action, e.g., a label indicating translation, rotation, etc. Similarly, if a machine learning model is being trained to classify ultrasound images on the basis of anatomical features in the ultrasound image, the ground truth output for the model may be a label indicating one or more anatomical features in the ultrasound image.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing system 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/ communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store a measurement model 208, a training module 210, and ultrasound image data 212. The measurement model 208 may include one or more machine learning models, such as deep learning networks, comprising a plurality of weights and biases, activation functions, loss functions, gradient descent algorithms, and instructions for implementing the one or more deep neural networks to process input ultrasound images. The measurement model 208 may include trained and/or untrained neural networks and may further include training routines, or parameters (e.g., weights and biases), associated with one or more neural network models stored therein.

The measurement model 208 may generate multiple outputs for a given ultrasound image. For example, the measurement model 208 may output an anatomy view 207 of an image, an image quality 209 of the image, a segmentation and measurement 211 of the image, and a disease risk or progression 213 based on the measurement. In one example, measurement model 208 may be a plurality of models, in which each output for a given ultrasound image may be generated by a separate model. In such examples, the measurement model may comprise an anatomy view model, an image quality model, a segmentation and measurement model, and a risk or progression model. In some examples, the output of one model may be used as input to another model or the output of one model may be evaluated to determine if the ultrasound image should be input into the other models. For example, the output from the anatomy view model and the image quality model may be evaluated to determine if the ultrasound image should be rejected or entered as input to the segmentation and measurement model.

The anatomy view 207 that is determined/output by the measurement model 208 may include a current anatomical view (e.g., a scan plane or an anatomical region) for a current ultrasound image. For example, if the ultrasound image includes a liver and/or is acquired as part of an abdominal scan, the measurement model 208 may be trained to determine if the input ultrasound image includes a target anatomy view of the liver/abdomen, such as the long axis aortal view. In some examples, the anatomy view 207 may also include anatomical features identified in the current ultrasound image. For example, the anatomical features may be identified in the current ultrasound image using segmentation, and then the identified anatomical features may be used to determine the scan plane/anatomical region that is imaged in the current ultrasound image. In some examples, in addition to identifying the current anatomical view, the measurement model may be trained to determine how close (e.g., in degrees and/or a distance measurement) the current anatomical view is to a standard or target view in which the measurement of the visceral fat is to occur. For example, if the target view is the long axis aortal view, the measurement model may be determined to identify if the current anatomical view is the long axis aortal view, and if so, how well the current view matches the standard long axis aortal view. The model may determine if the current view is tilted at some angle relative to the standard long axis aortal view (e.g., tilted at 5 degrees relative to the plane of the standard long axis aortal view) and if the current view is centered similarly or differently than the standard long axis aortal view (e.g., offset vertically and/or horizontally by a certain distance(s), such as vertically offset by 3 cm).

The image quality 209 that is determined/output by the measurement model 208 may include an indicator (visual or non-visual) that a current ultrasound image may be acceptable or unacceptable for visceral fat measurements. For example, if the ultrasound image includes a liver and/or is acquired as part of an abdominal scan, the measurement model 208 may be trained to determine if the input ultrasound image has a threshold image resolution, image contrast, noise, and/or brightness. Further, the image quality 209 as determined by the measurement model may be a function of the ability of the measurement model to segment and measure the visceral fat (explained below), and thus may be based on a sharpness of edges of specific anatomical features (e.g., the liver, the visceral fat, the linea alba, etc.), lack of artifacts in the image (particularly in the region where the measurement will be taken), lack of motion-induced blur, etc. In some examples, the image quality 209 output may include a quality metric, such as a numeric value on a scale of 1-10, and the numeric value may be compared to a quality or sufficiency threshold to determine if the image quality of the current image frame is high enough to accurately perform the measurement of the visceral fat, and this sufficiency threshold may be learned by the measurement model during training, as will be explained in more detail below. In some examples, the sufficiency threshold may be adjusted based on the current anatomy view, e.g., based on how close the current anatomy view is to the standard/target anatomy view.

The segmentation and measurement 211 that is determined/output by the measurement model 208 may include a measurement of visceral fat thickness of a current ultrasound image. For example, if the ultrasound image includes a liver and/or is acquired as part of an abdominal scan, the measurement model 208 may be trained to segment the ultrasound image and determine the visceral fat thickness of the ultrasound image. The segmentation performed by measurement model 208 may include determination and output of a visual indicator surrounding the visceral fat on a top side and a bottom side in the ultrasound image. In one example, measurement model 208 may output a visual indicator surrounding multiple sections of the ultrasound image for image clarity, such as on a top side and a bottom side of subcutaneous adipose tissue, linea alba, and/or a lobe of the liver in the ultrasound image. In one example, measurement model 208 may color segmented areas of the ultrasound image. Measurement model 208 may be trained to measure visceral fat thickness from a uniform position (e.g., along a central axis of the ultrasound image) to a uniform position of the ultrasound image. In one example, measurement model 208 may be trained to measure visceral fat thickness at a thickest point of the visceral fat in the ultrasound image. In another example, the measurement model 208 may be trained to measure the visceral fat thickness at a plurality of locations along the visceral fat and determine an average visceral fat thickness for a given image frame. In one example, measurement model 208 may be trained to measure visceral fat thickness across a plurality of frames and compute an average value.

The disease risk or progression 213 that is determined/output by the measurement model 208 may include a prediction value (e.g., a pictogram, a scale, a color mapping) indicating a prediction regarding the presence and/or progression of NAFLD from a current ultrasound image. For example, if the ultrasound image includes a liver and/or is acquired as part of an abdominal scan, the measurement model 208 may be trained to determine the risk of NAFLD being present and output the prediction as a value, a pictogram, a progression bar, a color mapping, or the like. In one example, recommendations for future actions (e.g., physician visits, scans) may be displayed as well as recommendations for when to schedule future actions based on the predictions made by measurement model 208. In one example, measurement model 208 may predict progression of NAFLD and possible outcomes for a patient if no future action is taken, if recommended future actions are taken, and the like.

Thus, the measurement model 208 may be one or more deep learning networks (e.g., neural networks) that take one or more ultrasound images as input and produces multiple outputs, including anatomical view, image quality, organ/anatomical feature segmentation and visceral fat measurement, and liver disease risk or progression. The network may be trained jointly with loss functions for all of these tasks. For the determination of the anatomy view that is determined/output by the measurement model, expert-provided labels/annotations may be used to train the measurement model and a respective suitable loss function will be added to the joint model being trained. The annotations may include an indication of the scan plane/anatomical features in each image, to train the model to determine the anatomy view. To segment and measure the visceral fat, the measurement model 208 may be trained with images annotated by expert clinicians (e.g., experts may measure the visceral fat in a plurality of images and the images may include a label indicating the measurement points between which the thickness of the visceral fat is determined and/or a value indicating the thickness of the visceral fat).

To determine the image quality, the measurement model 208 may be trained with a plurality of images at varying qualities. An expert clinician or a separate model (e.g., neural network) may select images or generate images at a purposefully reduced quality with annotations of acceptable or unacceptable image quality to train measurement model 208 on determining what factors into an acceptable or unacceptable image. In another example, the measurement model 208 may be trained to determine image quality using training data that includes a plurality of sets of images, each including a high quality image and a subset of images generated from the high quality image, each at a progressively lower quality (e.g., generated by an expert or automatically by another model, such as a neural network). The lower quality images may be generated by removing pixel information from the high quality images (e.g., removing progressively larger amounts of pixel information), introducing artifacts to the high quality images (or not compensating for artifacts within the image data of the high quality images), blurring edges of anatomical features within the high quality images, and so forth. Once the measurement model 208 has been trained to segment and measure the visceral fat, the purposefully reduced-quality images may be input into the partially trained measurement model 208, which may segment and the measure the visceral fat in the images. The measurement model 208 may output the measurement and compare the measurement to a ground truth measurement, which may be a measurement performed by an expert on the same image, but at a higher quality (e.g., before the quality was purposefully reduced). Alternatively, the measurement model 208 may perform a measurement on both the high quality image and all corresponding reduced quality images, and compare the measurements performed on the reduced quality images to the measurement performed on the high quality image (e.g., the measurement performed on the high quality image may be the ground truth measurement). If the measurement model 208 is unable to accurately measure the visceral fat on a given image, that image may be deemed to be of insufficient quality, and the model may learn which image features provide for sufficient versus insufficient quality. As an example, the model may be trained to output an image quality metric that indicates a relative level of image quality of an input image, and the model may also learn a sufficiency threshold to which the image quality metric may be compared to determine if the input image is of sufficient quality.

To determine the risk and/or progression of the liver disease, the measurement model 208 may be trained with historical data, in which previous ultrasound images with known and quantifiable risk and/or progression of NAFLD may be used for training risk/progression predictions based on a given visceral fat thickness. Images for training may be selected by an expert clinician to guide measurement model 208 towards recognizing historically frequent use cases as well as testing measurement model 208 on recognizing and responding to outliers and infrequent use cases. In some examples, the risk and/or progression of the liver disease may be determined further based on a patient's medical history and current demographic and/or risk factors, such as the patient's weight, age, sex, geographic location, diagnostic lab tests (e.g., blood test results), etc., which may be retrieved from the patient's electronic medical record. Thus, in some examples, in addition to the training data including ultrasound images labeled with visceral fat measurements and patient disease prognosis, the training data may further include patient medical history, demographics, blood (or other biological sample) test results, and/or risk factors.

Further, while the measurement model 208 has been described herein has using 2D ultrasound images as input, in some examples the measurement model 208 may use 3D ultrasound data instead of or in addition to 2D images. For example, the anatomy view and the anatomical feature segmentation (and visceral fat measurement) may be determined using 3D data. Further still, while the measurement model 208 has been described herein as being trained to analyze ultrasound images to determine liver disease risk or progression, a similar approach could be taken to evaluate liver disease for other imaging modalities, particularly handheld or otherwise easily manipulated imaging modalities, such as X-ray/fluoroscopy scanners, near infrared (NIR) spectroscopy scanners, and optical coherence tomography (OCT) scanners.

Non-transitory memory 206 may further include training module 210, which comprises instructions for training one or more of the machine learning models stored in the measurement model 208. In some embodiments, the training module 210 is not disposed at the image processing system 202. In such examples, the measurement model 208 thus includes trained and validated network(s).

Non-transitory memory 206 may further store ultrasound image data 212, such as ultrasound images captured by the ultrasound imaging system 100 of FIG. 1. The ultrasound images of the ultrasound image data 212 may comprise ultrasound images that have been acquired by the ultrasound imaging system 100 with different anatomical features (e.g., different amounts of visceral fat) and/or different image quality. Further, ultrasound image data 212 may store ultrasound images, ground truth output, iterations of machine learning model output, and other types of ultrasound image data that may be used to train the measurement model 208, when training module 210 is stored in non-transitory memory 206. In some embodiments, ultrasound image data 212 may store ultrasound images and ground truth output in an ordered format, such that each ultrasound image is associated with one or more corresponding ground truth outputs. However, in examples where training module 210 is not disposed at the image processing system 202, the images/ground truth output usable for training the measurement model 208 may be stored elsewhere.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

FIG. 3 is an example view 300 of a liver during an ultrasound exam. View 300 may include an ultrasound image 302 that is displayed on a display device (e.g., display device 234 of FIG. 2) with graphical representations of output of a measurement model, such as measurement model 208 of FIG. 2, in response to the ultrasound image being input to the measurement model. View 300 shows a segmentation of visceral fat 304 defined by a first line 306 on a top side of the visceral fat 304 (e.g., at the border between the visceral fat and the linea alba) and a second line 308 on a bottom side of the visceral fat 304 (e.g., at the border between the liver and the visceral fat). View 300 shows a visceral fat thickness measurement displayed in a graphical text box 310. In one example, view 300 may show visceral fat thickness measurements in a plurality of units (e.g., imperial, metric). View 300 may show a first measurement point 314 and a second measurement point 316 placed by the measurement model as well as a measurement line 312 spanning from the first measurement point 314 to the second measurement point 316, where first measurement point 314 may be a point on a top side of visceral fat 304, second measurement point 316 may be a point on a bottom side of visceral fat 304, and measurement line 312 may be a measured distance between first measurement point 314 and second measurement point 316. Measurement line 312 may be used to determine the thickness of visceral fat 304, represented in graphical text box 310. In one example, view 300 may show the visceral fat thickness measurement being taken along a central axis of the image, at a thickest part of the visceral fat, or the like.

For example, when the visceral fat measurement is computed at the thickest part of the visceral fat segmented region, the trained measurement model may segment the visceral fat region and then compute and auto-place measurement calipers at the thickest part of the segmented region (e.g., the first measurement point 314 and the second measurement point 316) and then compute the length of the thickest part of the visceral fat.

In addition, the measurement model may also be trained to segment the subcutaneous adipose tissue area, and based on the segmented region of the subcutaneous adipose tissue, two measurement calipers corresponding to the thickest region of the subcutaneous adipose tissue could be computed and automatically placed. The length between these calipers could be computed and displayed.

Therefore, in addition to visceral fat thickness measurement, two additional measurements could be automatically computed and displayed to the user: a) thickness of subcutaneous adipose tissue, and b) a ratio of thickness of subcutaneous adipose tissue to thickness of the visceral fat. In some examples, the user may select whether to view only the measurement of the visceral fat or whether to view the measurement of the visceral fat and the subcutaneous adipose tissue and/or ratio of the subcutaneous adipose tissue to thickness of the visceral fat.

FIG. 4 is another example view 400 including the ultrasound image 302 that is displayed on a display device (e.g., display device 234 of FIG. 2). View 400 shows the thickness measurement of visceral fat 304 displayed in the graphical text box 310, similar to the view 300 explained above. A prediction risk graphical element 404 may be displayed in view 400 showing a prediction of a presence of NAFLD output by the measurement model based on the thickness measurement of visceral fat 304. Prediction risk graphical element 404 may be displayed in view 400 as a partitioned bar with an indicator, wherein the indicator being on a left side of the partitioned bar represents a lower predicted risk of NAFLD being present and the indicator being a right side of the partitioned bar represents a higher predicted risk of NAFLD being present. The prediction risk displayed within graphical element 404 may be displayed in view 400 as text, including "LOW", "HIGH", and the like. The prediction risk may also be determined based on a plurality of patient data as well as visceral fat thickness, including but not limited to demographical patient data and patient medical data.

FIG. 5 is another example view 500 including the ultrasound image 302 that is displayed on a display device (e.g., display device 234 of FIG. 2). View 500 shows the thickness measurement of visceral fat 304 displayed in the graphical text box 310. A progression bar 504 may be displayed in view 500 showing a prediction of a progression of NAFLD in the liver as output by the measurement model. In the example shown, the progression bar 504 may include a gradient of color (e.g., black/white/gray) that changes (e.g., from light to dark) in correspondence to disease progression, and an arrow may be placed along the progression bar 504 to indicate a current estimated disease progression. In one example, view 500 may represent a view for a follow-up examination when NAFLD has already been identified in a patient, wherein progression bar 504 may represent a comparative measurement of NAFLD based on visceral fat thickness measurements from a current examination and a previous examination. While FIGS. 4 and 5 do not include the lines segmenting the visceral fat or the measurement line between the measurement points, it is to be understand that the lines segmenting the visceral fat and/or the measurement line between the measurement points may be displayed, similar to view 300 of FIG. 3.

Figure 6:
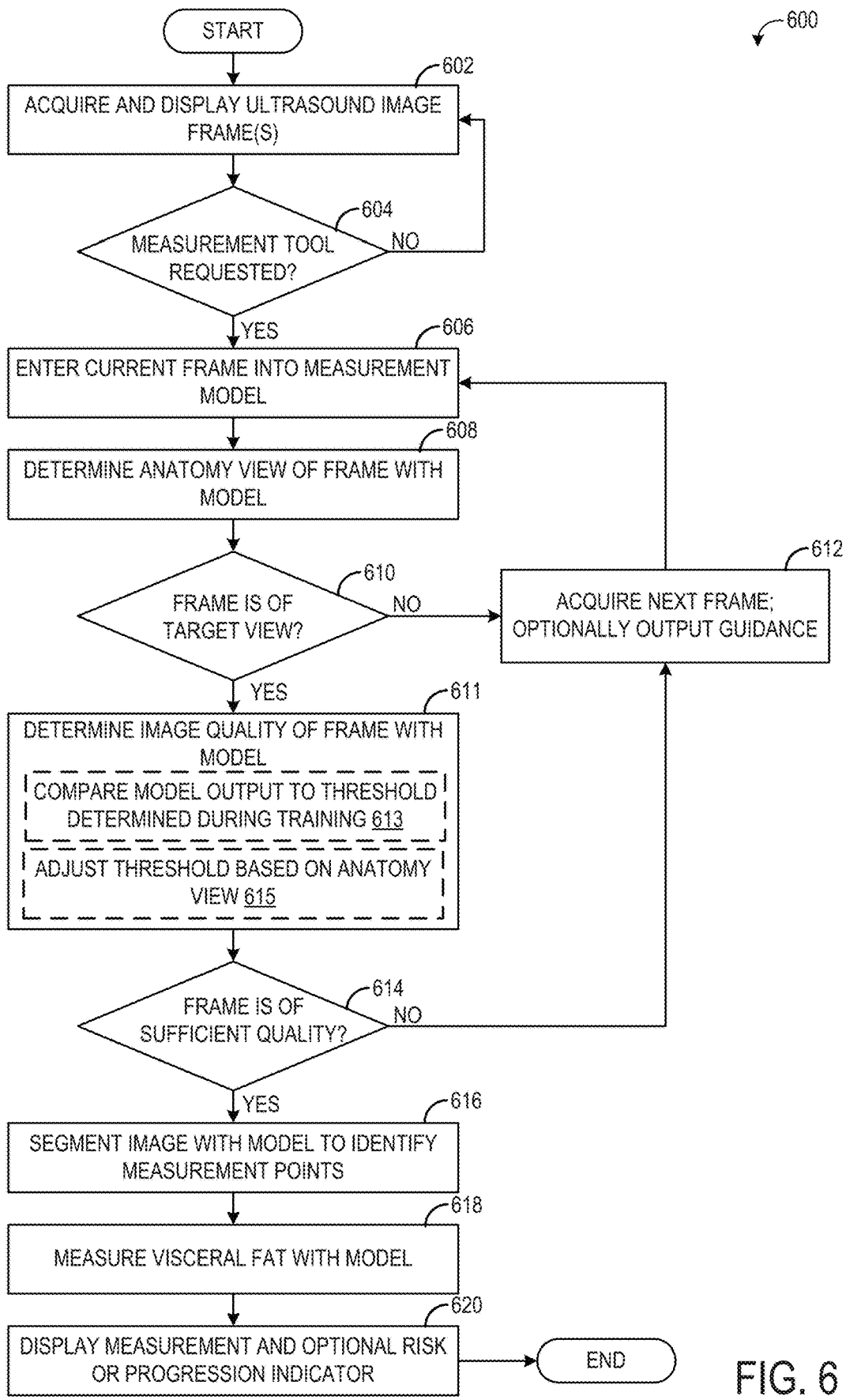
FIG. 6 is a flow chart illustrating an example method for evaluating liver disease using a measurement model.

FIG. 6 is a flow chart illustrating an example method 600 for a measurement model, such as measurement model 208 of FIG. 2, taking ultrasound images from a scan as input and displaying metrics of a liver disease, such as NAFLD, as output, according to an embodiment of the present disclosure. Method 600 is described with regard to the systems and components of FIGS. 1-2, though it should be appreciated that the method 600 may be implemented with other systems and components without departing from the scope of the present disclosure. Method 600 may be carried out according to instructions stored in non-transitory memory of a computing device, such as image processing system 202 of FIG. 2.

At 602, ultrasound images are acquired and displayed on a display device. For example, the ultrasound images of a subject may be acquired with the ultrasound probe 106 of FIG. 1 and displayed to an operator via display device 118. The images may be acquired and displayed in real time or near real time, and may be acquired with default or user-specified scan parameters (e.g., default depth, frequency, etc.).

At 604, the method 600 includes determining if a measurement tool configured to measure visceral fat as a marker for the liver disease has been requested. The measurement tool may include a measurement model, such as the measurement model 208 of FIG. 2, as well as instructions to implement the model on one or more ultrasound images and make decisions/process the output of the measurement model. The measurement tool may be requested by an operator via a user input (e.g., by pressing a button or selecting a user interface control button) during the ultrasound scanning. If the measurement tool is not requested, method 600 may continue to 602 to acquire more ultrasound images.

If the measurement tool has been requested at 604, method 600 may continue to 606, which includes entering a current image frame into a measurement model. In one example, the measurement model is measurement model 208 of FIG. 2, and thus includes an anatomy view output, such as anatomy view 207 of FIG. 2, an image quality output, such as image quality 209 of FIG. 2, a segmentation and measurement output, such as segmentation and measurement 211 of FIG. 2, and a disease risk or progression output, such as disease risk or progression 213 of FIG. 2.

At 608, the method 600 includes determining an anatomy view of the current frame with the measurement model. The measurement model may determine the anatomy view as described above with respect to FIG. 2. For example, the current image frame may be input to the measurement model, which may be trained to determine if the current frame is at a target view where specific anatomical features (e.g., the liver, the linea alba) are present at a specific cross-section and/or orientation. As an example, the target view may include the long axis aortal view or another suitable view.

At 610, the method 600 includes determining if the current frame is of the target view. In some examples, the measurement model may output a binary indicator of the anatomy view. For example, the measurement model may output an indication of whether the anatomy view of the current frame is the target view (e.g., a yes or no). In other examples, the measurement model may output the name of the anatomy view of the current frame, and the measurement tool may decide if the anatomy view matches the target view. In some examples, the measurement model may also output a confidence score that reflects how close/similar the anatomy view of the current frame is to the target view.

If the current frame is not of the target view at 610, method 600 may continue to 612, which includes acquiring a next frame in the ultrasound images. In this way, the measurement may not be performed if the current image frame is not the target/standard view. In one example, guidance may be output (e.g., displayed on the display device) before the next frame is acquired, indicating the factors or parameters regarding the current frame not being of target view and/or how to acquire a frame of the target view. In some examples, rather than analyzing the current frame and then guiding the operator to acquire another frame, the measurement tool may be configured to analyze one or more additional image frames saved in memory. In one example, if no frames in a scan are of target view, guidance may be displayed on how to acquire target view frames for a subsequent scan. Further, while method 600 is described herein as being implemented during an examination of a patient that is in process, the measurement tool may be requested after an exam has been performed and the images may be retrieved from an image archive (e.g., a PACS) and entered into the measurement model. Method 600 may continue to 606 to enter the next frame into the measurement model (e.g., whether the next frame is acquired subsequent the current frame, or is another frame/image from a complete exam).

If the current frame is of the target view at 610, method 600 proceeds to 611 to determine the image quality of the current frame with the model. As explained above with respect to FIG. 2, the measurement model may output an image quality metric (e.g., a numeric value) that indicates a relative image quality of the current frame, and this quality metric may be compared to a sufficiency threshold that is determined during training of the measurement model, as indicated at 613. For example, the image quality metric may be a numeric value on a scale of 1-10 and the sufficiency threshold may be a non-zero numeric value between 1-10, such as 7. If the image quality metric of the current frame is above the sufficiency threshold, the current frame may be determined to be of sufficient quality to perform the visceral fat measurement, as described below. In some examples, the sufficiency threshold may be adjusted based on the anatomy view of the current frame, as indicated at 615. For example, as explained above, the measurement model may be trained to output a confidence score when evaluating the anatomy view of the current frame, where the confidence score (e.g., on a scale of 0-100) indicates how sure the model is that the current anatomy view is the target view and/or how close the current anatomy view is to the target view. If the confidence score of the current frame is within a threshold range (e.g., below an upper threshold but above a lower threshold, such as within 80-90), the sufficiency threshold may be adjusted (e.g., increased). In this way, when the current frame is at or very close to the target view (e.g., the confidence score is above the threshold range), a relatively lower sufficiency threshold may be applied, where if the current frame is somewhat close to the target view (e.g., within the threshold range), a higher sufficiency threshold may be applied. In doing so, accurate measurements of the visceral fat may be ensured while allowing for some flexibility in variations in the anatomy view or image quality (but not both) of the current frame, which may increase the number of images that may qualify for the visceral fat measurement and lower the total number of images that need to be acquired to perform an accurate measurement.

At 614, method 600 includes determining if the current frame is of sufficient image quality, for example if the quality metric of the current frame as output by the model is greater than the sufficiency threshold. If the current frame is not of sufficient quality (e.g., the image quality metric is below the sufficiency threshold), method 600 proceeds to 612 to acquire or obtain the next frame and optionally provide guidance for the acquisition of the next frame. If the current frame is of sufficient quality (e.g., the image quality metric is above the sufficiency threshold), method 600 proceeds to 616, which includes segmenting the current frame with the measurement model to identify measurement points. Segmenting the current frame may include identifying the visceral fat, including indicating a top side of visceral fat and a bottom side of visceral fat in the current frame. Measurement points may include a first measurement point and a second measurement point on a top side and a bottom side of the visceral fat, respectively. Measurement points may be placed along a central vertical axis of the current frame, where the first measurement point may be placed where the top side of visceral fat intersects with the central vertical axis and the second measurement point may be placed where the bottom side of visceral fat intersects with the central vertical axis. In one example, a plurality of measurement point pairs may be used when the measurement model is configured to measure visceral fat thickness in multiple places to calculate an average visceral fat thickness.

At 618, the method 600 includes measuring visceral fat with the measurement model. Measuring visceral fat thickness may include measuring a distance from the first measurement point to the second measurement point. In one example, multiple measurement point pairs may be used such that multiple measurements of visceral fat thickness may be taken.

At 620, the method 600 includes displaying a measurement of visceral fat thickness and optionally displaying a risk or progression indicator. The measurement may be determined by the measurement model and displayed on one or more display devices (e.g., a computer monitor) in the form of text displaying the value and units of the measurement and a graphical indicator of the measurement illustrating the measurement points and the measurement between the measurement points (e.g., overlaid on the visceral fat in the image). The disease risk or progression may be determined by the measurement model and displayed on of the one or more display devices. In other examples, the measurement tool may determine the risk or progression based on the output of the measurement model (e.g., the visceral fat thickness) as well as patient data (e.g., demographics, risk factors, medical history) and/or past measurements of visceral fat thickness according to a set of rules or another suitable mechanism. The disease risk or progression may be displayed as text, such as indicating an assessment of a likelihood of NAFLD being present, displayed as a graphical bar, such as indicating an assessment of a progression of NAFLD where a first end of the graphical bar represents little to no progression and a second end of the graphical bar represents significant progression, or displayed as a combination of text and graphical indicators. In one example, a patient may receive comparative results during a second or third examination where a current disease risk or progression assessment may be displayed alongside or in relation to a previous disease risk or progression assessment. Method 600 then ends.

In this way, method 600 may be performed in order to provide an indication of whether a patient undergoing an ultrasound examination may be at risk of having a liver disease such as NAFLD. NAFLD is defined by diffusely distributed fat throughout the liver. Measuring the fat content of the liver cells gives a direct diagnosis, but it is technically a very challenging task. By contrast, visceral fat is measured as disclosed herein, which is a "marker" for fatty liver disease (i.e., excessive visceral fat correlates with excessive fat in the liver but it is not a direct determination). Visceral fat is the fat deep inside the abdominal region of the body that wraps around the kidneys and other abdominal organs (e.g., stomach, intestines). Visceral fat measurements may be performed faster and easier than other methods of diagnosing NAFLD using ultrasound and may be performed in a fully automatic manner Measuring visceral fat thickness does not demand expensive or special hardware/equipment, such as equipment that is used in shearwave/fibroscan techniques. Likewise, measuring visceral fat does not demand special technical skills or training from the users. Thus, relying on the measurement of the visceral fat is a cheap, simple, non-invasive, and scalable way to screen populations for NAFLD, and may be particularly valuable for pediatric patients.

Figure 7:
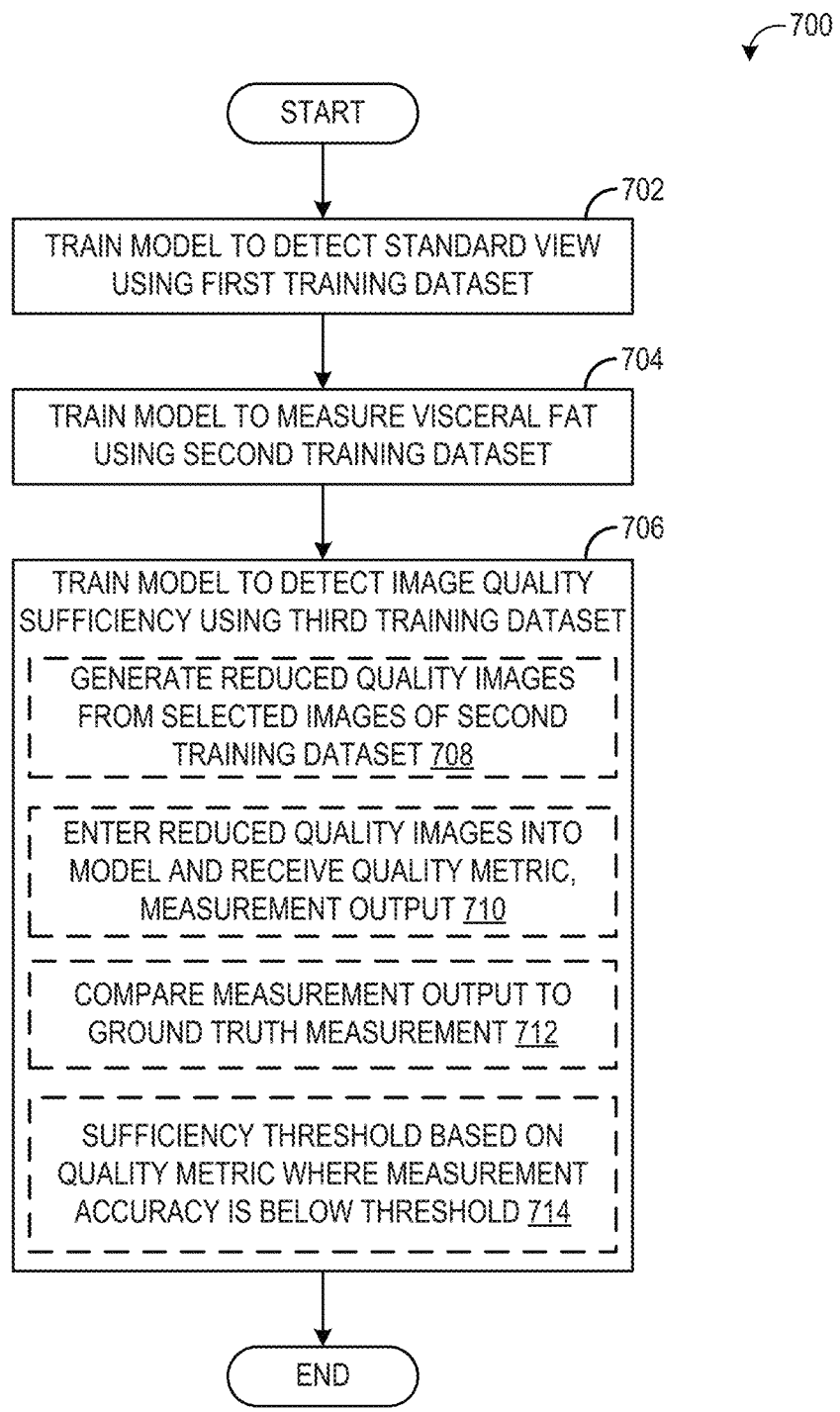
FIG. 7 is a flow chart illustrating an example method for training a measurement model.

FIG. 7 is a flow chart illustrating an example method 700 for training a measurement model, such as measurement model 208 of FIG. 2, according to an embodiment of the present disclosure. Method 700 is described with regard to the systems and components of FIGS. 1-2, though it should be appreciated that the method 700 may be implemented with other systems and components without departing from the scope of the present disclosure. Method 700 may be carried out according to instructions stored in non-transitory memory of a computing device, such as training module 210 of image processing system 202 of FIG. 2.

At 702, the method 700 includes training the measurement model to detect a standard or target anatomical view using a first training dataset. The first training dataset may include a plurality of ultrasound images annotated by an expert to indicate whether an image is a correct standard anatomical view or not (e.g., the target anatomical view explained above). In another example, the first training dataset may include a plurality of images of various anatomical views, with each image labeled with a corresponding anatomical view by an expert.

At 704, the method 700 includes training the measurement model to measure visceral fat using a second training dataset. The second training dataset may include a plurality of ultrasound images annotated by an expert with visceral fat measurements. The measurement model may be trained by measuring visceral fat from known measurement points and comparing the measurement to a known measurement for the image. The measurement model may also be trained by measuring visceral fat using measurement points placed by the measurement model instead of known measurement points to compare an accuracy of the measurement as well as an accuracy of the placement of measurement points.

At 706, the method 700 includes training the measurement model to detect image quality sufficiency using a third training dataset. The third training dataset may include a plurality of ultrasound images annotated with indications of sufficient or insufficient image quality. The third training dataset may include high quality images so the measurement model may identify qualities of a high quality image (e.g., high contrast to noise ratio, high resolution). The third training dataset may also include images of lower quality so the measurement model may identify qualities of an image of insufficient image quality.

In some examples, as at 708, training the measurement model to detect image quality sufficiency includes generating images of reduced quality from selected images of the second training dataset. A plurality of images of decreasing quality may be included, varying from images that are less significant in quality reduction to images that are more significant in quality reduction, and these images may comprise the third training dataset. In this example, the images may be labeled with a predetermined indication of the image quality, such as a quality metric. For example, the original image may be labeled with a 10 (indicating the highest quality) and each purposely reduced image generated from the original image may be labeled based on the level of quality reduction (e.g., a first image may be labeled with a 9, indicating somewhat reduced quality while a second image may be labeled with a 5, indicating a significant reduction in quality).

In some examples, as at 710, training the measurement model to detect image quality sufficiency includes entering the original images and the images of reduced quality, such as those generated at 708, into the measurement model and receiving a measurement output for each image from the measurement model. The measurement model may be trained to perform the visceral fat measurements as explained above.

In some examples, as at 712, training the measurement model to detect image quality sufficiency includes comparing each measurement output from 710 to a respective ground truth measurement. The ground truth measurements may be the measurements performed by the measurement model on the original high quality images (e.g., before the reduction in quality described above) or measurements performed on the high quality images by an expert. The measurements from the measurement model at 710 may be compared to ground truth measurements for each image, where an absolute value of error between a measurement from the measurement model and the corresponding ground truth measurement may be compared to an accuracy threshold, for each image. The accuracy threshold may be used to determine which measurements from the measurement model are not accurate, e.g., if the absolute value of error exceeds the accuracy threshold for an image.

In some examples, as at 714, training the measurement model to detect image quality sufficiency includes determining a sufficiency threshold of image quality based on an image quality of images where a measurement accuracy of the measurement output from 710 is below the accuracy threshold. Using the accuracy threshold, a level of image quality reduction may be identified where the measurement model may still make accurate measurements satisfying the accuracy threshold, and the model may learn a lowest level of image quality where the measurement model is still able to make accurate measurements by the accuracy threshold. As explained above with respect to FIG. 6, the model may thus be trained to output an image quality metric for an input image and compare that quality metric to the sufficiency threshold to determine if the image is of sufficient quality for performing the measurement of the visceral fat. Method 700 then ends.

A technical effect of measuring visceral fat to predict or diagnose a presence of NAFLD using the measurement model described herein is that an NAFLD diagnosis, risk, or progression may be provided without an invasive medical procedure, in a fast and inexpensive manner Another technical effect of the measurement model is that the image plane and the quality of the images used for the visceral fat measurements may be standardized, which may increase the accuracy of the measurement.

The disclosure also provides support for a method for evaluating a liver disease of a subject, comprising: in response to a request to evaluate the liver disease, determining, with a measurement model, that a selected medical image frame of the subject includes a target anatomical view and has an image quality above an image quality threshold, and in response, measuring, with the measurement model, a marker for the liver disease in the selected medical image frame, and outputting, for display on a display device, a measurement of the marker. In a first example of the method, the method further comprises: determining, with the measurement model, that a prior medical image frame of the subject acquired before the selected medical image frame does not include the target anatomical view and/or does not have an image quality above the image quality threshold, and in response, rejecting the prior medical image frame such that the marker is not measured. In a second example of the method, optionally including the first example, the measurement model comprises one or more deep learning networks and wherein determining that the selected medical image frame includes the target anatomical view and has an image quality above the image quality threshold comprises entering the selected medical image frame into one or more of the one or more deep learning networks, where the one or more deep learning networks are trained to output an anatomical view of the selected medical image frame and an image quality of the selected medical image frame. In a third example of the method, optionally including one or both of the first and second examples, measuring the marker of the liver disease comprises entering the selected medical image frame into the one or more deep learning networks, where the one or more deep learning networks are trained to segment the selected medical image frame in order to identify the marker and measure the identified marker. In a fourth example of the method, optionally including one or more or each of the first through third examples, the image quality threshold is learned by the one or more deep learning networks during training. In a fifth example of the method, optionally including one or more or each of the first through fourth examples, to learn the image quality threshold and to output the image quality, the one or more deep learning networks are trained with a training dataset that includes a plurality of sets of medical image frames, each including a high quality image frame and a subset of image frames generated from the high quality image frame, each at a progressively lower quality. In a sixth example of the method, optionally including one or more or each of the first through fifth examples, the liver disease is non-alcoholic fatty liver disease, wherein the marker is visceral fat surrounding a liver, and wherein the measurement model is trained to measure a thickness of the visceral fat. In a seventh example of the method, optionally including one or more or each of the first through sixth examples, the method further comprises: determining a risk that the subject has the liver disease or a current progression of the liver disease in the subject based on the measurement of the marker, and outputting, for display, a visual representation of the risk or the progression.

The disclosure also provides support for a system, comprising: a display device, and an image processing system configured with instructions in non-transitory memory that when executed cause the image processing system to: determine if an ultrasound image frame of a subject includes a target anatomical view and if an image quality of the ultrasound image frame is above a threshold image quality, if the ultrasound image frame includes the target anatomical view and has an image quality that is above the threshold image quality, enter the ultrasound image frame into a measurement model trained to measure a thickness of visceral fat present in the ultrasound image frame, and output, for display on the display device, the measurement of the thickness of the visceral fat and an assessment of a liver disease of the subject that is determined based on the measurement of the visceral fat. In a first example of the system, the threshold image quality is learned by a deep learning network during training of the deep learning network, and wherein determining if the image quality of the ultrasound image frame is above the threshold image quality includes entering the ultrasound image frame as input to the deep learning network, wherein the deep learning network is trained to output the image quality. In a second example of the system, optionally including the first example, to learn the threshold image quality and to output the image quality, the deep learning network is trained with a training dataset that includes a plurality of sets of ultrasound image frames, each including a high quality image frame and a subset of image frames generated from the high quality image frame, each at a progressively lower quality. In a third example of the system, optionally including one or both of the first and second examples, determining if the ultrasound image frame includes the target anatomical view includes entering the ultrasound image frame as input to a deep learning network, wherein the deep learning network is trained to output an anatomical view of the ultrasound image frame and a confidence score that the anatomical view of the ultrasound image frame is the target anatomical view. In a fourth example of the system, optionally including one or more or each of the first through third examples, the instructions are executable to adjust the threshold image quality based on the confidence score. In a fifth example of the system, optionally including one or more or each of the first through fourth examples, the assessment of the liver disease includes a graphical indication of a risk of having the liver disease or a current progression of the liver disease, wherein the liver disease is non-alcoholic fatty liver disease.

The disclosure also provides support for a method for evaluating a liver disease of a subject, comprising: in response to a request to evaluate the liver disease, determining, with a measurement model, that a selected ultrasound image of the subject includes a target anatomical view and has an image quality that is sufficient for performing a measurement of visceral fat in the selected ultrasound image, and in response, measuring, with the measurement model, a thickness of the visceral fat in the selected ultrasound image, where the measurement model is trained to determine that the image quality is sufficient for performing the measurement of the visceral fat using a training dataset that comprises a plurality of subsets of images, each subset of images comprising an initial image and one or more reduced quality images generated from the initial image, and outputting, for display on a display device, the measurement of the thickness of the visceral fat. In a first example of the method, the measurement model is trained to output an image quality metric indicating the image quality of the selected ultrasound image and determine that the image quality is sufficient based on the image quality metric being greater than a sufficiency threshold, wherein the sufficiency threshold is learned by the measurement model using the training dataset. In a second example of the method, optionally including the first example, the method further comprises: determining a risk that the subject has the liver disease or a current progression of the liver disease in the subject based on the measurement, and outputting, for display, a visual representation of the risk or the progression. In a third example of the method, optionally including one or both of the first and second examples, the liver disease is non-alcoholic fatty liver disease. In a fourth example of the method, optionally including one or more or each of the first through third examples, the measurement model comprises one or more deep learning networks. In a fifth example of the method, optionally including one or more or each of the first through fourth examples, measuring, with the measurement model, the thickness of the visceral fat in the selected ultrasound image comprises entering the selected ultrasound image as input to the measurement model, the measurement model trained to segment the selected ultrasound image to identify the visceral fat, place measurement points on borders of the visceral fat, and determine the thickness by measuring a distance between the measurement points.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:
1. A system, comprising:
a display device; and an image processing system configured with instructions in non-transitory memory that when executed cause the image processing system to:
determine, based on a first output of a measurement model and a second output of the measurement model, if an ultrasound image frame of a subject includes a target anatomical view and if an image quality of the ultrasound image frame is above a threshold image quality;
if the ultrasound image frame includes the target anatomical view and has an image quality that is above the threshold image quality, obtain, from the measurement model, a measurement of a thickness of visceral fat present in the ultrasound image frame; and
output, for display on the display device, the measurement of the thickness of the visceral fat and an assessment of a liver disease of the subject that is determined based on the measurement of the visceral fat, wherein the measurement model includes one or more deep learning networks that are configured to take the ultrasound image frame as input and produce multiple outputs, including the first output indicating if the ultrasound image frame includes the target anatomical view, the second output indicating the image quality of the ultrasound image frame, and a third output including the measurement of the thickness of the visceral fat, wherein the measurement model is trained to generate the second output after the measurement model is trained to generate the third output, and wherein training the measurement model to generate the second output includes entering a plurality of training ultrasound images of varying quality to the measurement model, determining an accuracy of measured visceral fat of each training ultrasound image, and updating the measurement model based on the accuracy.

2. The system of claim 1, wherein the threshold image quality is learned by a first deep learning network of the one or more deep learning networks during training of the first deep learning network, wherein determining if the image quality of the ultrasound image frame is above the threshold image quality includes entering the ultrasound image frame as input to the first deep learning network, wherein the first deep learning network is trained to produce the first output, and wherein the first output includes the image quality.

3. The system of claim 2, wherein the plurality of training ultrasound images of varying quality includes a plurality of sets of ultrasound image frames, each including a higher quality image frame and a subset of image frames generated from the higher quality image frame, each at a progressively lower quality than the higher quality image frame, and wherein to produce the third output, a second deep learning network of the one or more deep learning networks is trained to segment the visceral fat in the ultrasound image frame and measure the thickness of the segmented visceral fat at one or more measurement points.

4. The system of claim 1, wherein determining if the ultrasound image frame includes the target anatomical view includes entering the ultrasound image frame as input to a second deep learning network of the one or more deep learning networks, wherein the second deep learning network is trained to produce the second output, and wherein the second output includes an anatomical view of the ultrasound image frame and a confidence score that the anatomical view of the ultrasound image frame is the target anatomical view.

5. The system of claim 4, wherein the instructions are executable to adjust the threshold image quality based on the confidence score, and wherein the target anatomical view is a long axis aortal view of the liver.

6. The system of claim 1, wherein the assessment of the liver disease includes a graphical indication of a risk of having the liver disease or a current progression of the liver disease, wherein the liver disease is non-alcoholic fatty liver disease.

* * * * *